United States Patent
Delaroche et al.

(10) Patent No.: US 10,351,814 B2
(45) Date of Patent: Jul. 16, 2019

(54) METHOD FOR THE INDUSTRIAL PRODUCTION OF FLOUR FROM LIPID-RICH MICROALGA BIOMASS WITH NO "OFF-NOTES" BY CONTROLLING THE OXYGEN AVAILABILITY

(71) Applicant: Corbion Biotech, Inc., South San Francisco, CA (US)

(72) Inventors: Sylvain Delaroche, Longuenesse (FR); Marie Le Ruyet, Lille (FR); Laurent Segueilha, Marquette lez Lille (FR); Heike Jerosch, Estaires (FR); Amandine Druon, Lille (FR)

(73) Assignee: CORBION BIOTECH, INC., South San Francisco, CA (US)

( * ) Notice: Subject to any disclaimer, the term of this patent is extended or adjusted under 35 U.S.C. 154(b) by 0 days.

(21) Appl. No.: 14/913,383

(22) PCT Filed: Aug. 22, 2014

(86) PCT No.: PCT/FR2014/052113
§ 371 (c)(1),
(2) Date: Feb. 22, 2016

(87) PCT Pub. No.: WO2015/025111
PCT Pub. Date: Feb. 26, 2015

(65) Prior Publication Data
US 2016/0208212 A1 Jul. 21, 2016

(30) Foreign Application Priority Data

Aug. 23, 2013 (FR) ...................................... 13 58144
Sep. 5, 2013 (FR) ...................................... 13 58521
Nov. 22, 2013 (FR) ...................................... 13 61520

(51) Int. Cl.
*C12N 1/12* (2006.01)
*C12P 7/64* (2006.01)
*A23L 17/60* (2016.01)

(52) U.S. Cl.
CPC ................ *C12N 1/12* (2013.01); *A23L 17/60* (2016.08); *C12P 7/6463* (2013.01); *A23V 2002/00* (2013.01)

(58) Field of Classification Search
None
See application file for complete search history.

(56) References Cited

U.S. PATENT DOCUMENTS

| | | |
|---|---|---|
| 2,949,700 A | 8/1960 | Kathrein |
| 3,108,402 A | 10/1963 | Kathrein |
| 3,142,135 A | 7/1964 | Kathrein |
| 4,564,526 A | 1/1986 | Takashima |
| 5,547,699 A | 8/1996 | Iizuka et al. |
| 5,792,631 A | 8/1998 | Running |
| 5,912,113 A | 6/1999 | Nakamura et al. |
| 2007/0099280 A1 | 5/2007 | Barclay |
| 2007/0167396 A1 | 7/2007 | Dillon et al. |
| 2010/0297295 A1 | 11/2010 | Brooks et al. |
| 2010/0297323 A1 | 11/2010 | Brooks et al. |
| 2010/0303989 A1 | 12/2010 | Brooks et al. |
| 2011/0293785 A1* | 12/2011 | Franklin .................. A23D 7/00 426/61 |
| 2013/0122180 A1 | 5/2013 | Brooks et al. |
| 2016/0046900 A1 | 2/2016 | MacQuart et al. |
| 2016/0192691 A1 | 7/2016 | Druon et al. |
| 2016/0324167 A1 | 11/2016 | Brooks et al. |
| 2016/0326483 A1 | 11/2016 | Segueilha et al. |
| 2016/0340640 A1 | 11/2016 | MacQuart et al. |
| 2016/0376544 A1 | 12/2016 | Cossart et al. |
| 2018/0139994 A1 | 5/2018 | Brooks et al. |
| 2018/0230421 A1 | 8/2018 | MacQuart et al. |

FOREIGN PATENT DOCUMENTS

| | | |
|---|---|---|
| CN | 101230364 A | 7/2008 |
| CN | 102618431 | 8/2012 |
| EP | 1 724 357 | 11/2006 |
| EP | 2 248 906 | 11/2010 |
| FR | 1356113 | 3/1964 |
| FR | 2 924 126 A1 | 5/2009 |
| JP | 360075244 | 10/1983 |
| JP | 409252707 A | 9/1997 |
| WO | WO 91/18108 | 11/1991 |
| WO | WO 2010/045368 | 4/2010 |
| WO | WO 2010/120923 | 10/2010 |
| WO | WO 2012/063137 | 5/2012 |

(Continued)

OTHER PUBLICATIONS

Syrett, P.J. 1953. The assimilation of ammonia by nitrogen-starved cells of Chlorella vulgaris. Part I. The correlation of assimilation with respiration. Annals of Botany 17(65): 1-19. specif. pp. 1, 2, 17.*

Zeng, A.-P. et al. 1994. Use of respiratory quotient as a control parameter for optimum oxygen supply and scale-up of 2,3-butanediol production under microaerobic conditions. Biotechnology and Bioengineering 44: 1107-1114. specif. pp. 1107, 1112, 1113.*

Mattes, R.D. 2009. Is there a fatty acid taste? Annual Review of Nutrition 29: 305-327; cited pre-pub manuscript, pp. 1-24. specif. p. 7.*

Chacon-Lee, T.L. et al. 2010. Microalgae for "healthy" foods—possibilities and challenges. Comprehensive Reviews in Food Science and Food Safety 9: 655-675. specif. pp. 655, 656, 658, 660, 669, 670.*

(Continued)

*Primary Examiner* — Renee Claytor
*Assistant Examiner* — Sharon M. Papciak
(74) *Attorney, Agent, or Firm* — Weaver Austin Villeneuve & Sampson LLP

(57) ABSTRACT

The invention relates to a method for fermentative production, on an industrial scale, of lipid-rich biomass of microalgae of the *Chlorella* genus having acceptable sensory properties, characterized in that the dissolved oxygen availability in the fermenter is controlled by tracking the respiratory quotient of said microalgae.

13 Claims, 3 Drawing Sheets

(56) References Cited

FOREIGN PATENT DOCUMENTS

| WO | WO-2012106751 A1 * | 8/2012 | ............ A61K 8/553 |
|---|---|---|---|
| WO | WO 2014/074769 | 5/2014 | |
| WO | WO 2014/154787 | 10/2014 | |
| WO | WO 2014/207376 | 12/2014 | |
| WO | WO 2014/207377 | 12/2014 | |
| WO | WO 2015/011428 | 1/2015 | |
| WO | WO 2015/022469 | 2/2015 | |
| WO | WO 2015/025111 | 2/2015 | |
| WO | WO 2015/079182 | 6/2015 | |
| WO | WO 2015/107312 | 7/2015 | |
| WO | WO 2017/137668 | 8/2017 | |

OTHER PUBLICATIONS

Albuquerque, M.G.E. et al. 2007. Strategies for the development of a side stream process for polyhydroxyalkanoate (PHA) production from sugar cane molasses. Journal of Biotechnology 130: 411-421. specif. pp. 412, 415, 417.*

Kliphuis, A.M.J. et al. 2011. Light respiration in Chlorella sorokiniana. Journal of Applied Phycology 23: 935-947. specif. pp. 935, 937, 938, 945.*

Abdel-Baky, H.H. et al. 2002. Volatile compounds of the microalga Chlorella vulgaris and their phytotoxic effect. Pakistan Journal of Biological Sciences 5(1): 61-65. specif. pp. 61, 63.*

Chen, Y.H., et al., "Fed-batch fermentation and supercritical fluid extraction of heterotrophic microalgal Chlorella protothecoides lipids," Bioresource Technology, Jun. 1, 2012, vol. 114, pp. 512-517.

Harms, P., et al., "Bioprocess monitoring," Current Opinion in Biotechnology, Apr. 1, 2002, vol. 13, No. 2, pp. 124-127.

Li, X., et al., "Large-Scale Biodiesel Production From Microalga Chlorella protothecoides Through Heterotrophic Cultivation in Bioreactors," Biotechnology and Bioengineering, Nov. 1, 2007, vol. 98, No. 4, pp. 764-771.

Suh, I.S., et al., "Photobioreactor Engineering: Design and Performance," Biotechnology and Bioprocess Engineering, Jan. 1, 2003, vol. 8, No. 6, pp. 313-321.

Xiong, W., et al., "High-density fermentation of microalga Chlorella protothecoides in bioreactor for microbio-diesel production," Applied Microbiology and Biotechnology, Dec. 6, 2007, vol. 78, No. 1, pp. 29-36.

Xu, H., et al., "High quality biodiesel production from a microalga Chlorella protothecoides by heterotrophic growth in fermenters," Journal of Biotechnology, Dec. 1, 2006, vol. 126, No. 4, pp. 499-507.

Written Opinion in International Application No. PCT/FR2014/052113, dated Nov. 20, 2014, pp. 1-6.

Non-Final Rejection, dated Jan. 11, 2017, in U.S. Appl. No. 14/779,365.

Final Rejection, dated Sep. 14, 2017, in U.S. Appl. No. 14/779,365.

Non-Final Rejection, dated Jul. 28, 2017, in U.S. Appl. No. 14/911,078.

Final Rejection, dated Jan. 26, 2018, in U.S. Appl. No. 14/911,078.

Restriction Requirement, dated Oct. 30, 2017, in U.S. Appl. No. 14/911,743.

Non-Final Rejection, dated Jan. 13, 2017, in U.S. Appl. No. 15/039,428.

Final Rejection, dated Jul. 11, 2017, in U.S. Appl. No. 15/039,428.

Non-Final Rejection, dated Jan. 5, 2018, in U.S. Appl. No. 15/039,428.

Non-Final Rejection, dated Apr. 6, 2017, in U.S. Appl. No. 15/112,436.

Final Rejection, dated Oct. 16, 2017, in U.S. Appl. No. 15/112,436.

Restriction Requirement, dated Jan. 19, 2017, in U.S. Appl. No. 15/112,436.

International Search Report, dated Sep. 30, 2014, from International Patent Application No. PCT/EP2014/056125, pp. 1-8.

Written Opinion of the Searching Authority, dated Sep. 30, 2014, from International Patent Application No. PCT/EP2014/056125, pp. 1-8.

International Search Report, for International Patent Application No. PCT/FR2014/051589, dated Oct. 6, 2014, pp. 1-10 (with English Translation pp. 1-15).

International Search Report, dated Nov. 24, 2014, from International Patent Application No. PCT/FR2014/051943.

Written Opinion of the Searching Authority, dated Nov. 24, 2014, from International Patent Application No. PCT/FR2014/051943.

International Search Report, dated Feb. 11, 2015, from International Patent Application No. PCT/FR2014/052081.

Written Opinion of the Searching Authority, dated Feb. 11, 2015, from International Patent Application No. PCT/FR2014/052081.

International Search Report, dated Nov. 20, 2014, from International Patent Application No. PCT/FR2014/052113.

International Search Report, dated Mar. 10, 2015, from International Patent Application No. PCT/FR2014/053075.

Written Opinion of the Searching Authority, dated Mar. 10, 2015, from International Patent Application No. PCT/FR2014/053075.

International Search Report, dated Jun. 1, 2015, for International Patent Application No. PCT/FR2015/050123, pp. 1-14.

Written Opinion, dated Jun. 1, 2015, for International Patent Application No. PCT/FR2015/050123, pp. 1-14.

International Search Report, dated Sep. 5, 2016, from International Patent Application No. PCT/FR2016/050269, filed Feb. 8, 2016, and English Translation.

Written Opinion of the Searching Authority, dated Sep. 5, 2016, from International Patent Application No. PCT/FR2016/050269, filed Feb. 8, 2016. No Translation.

Becker, E.W., "Micro-algae as a source of protein," Biotechnology Advances,vol. 25; No. 2, pp. 207-201, (Jan. 26, 2007).

Belasco, Warren, "Algae Burgers for a Hungry World? The Rise and Fall of Chlorella Cuisine," Technology and Culture, 38(3):608-634, (1997).

Brown, M.R., et al. "Biochemical composition of microalgae from the green algal classes Chlorophyceae and Prasinophycae. 1. Amino acids, sugars and pigments" Journal of Experimental Marine Biology and Ecology, Oct. 1, 1992, pp. 91-113, vol. 161 , No. 1.

Doucha , J. et al., "Production of High-density Chlorella culture grown in fermenters", Journal of Applied Phycology, Jan. 12, 2011 , vol. 24, No. 1, pp. 35-43.

Guccione, Alessia et al., "Chlorella for protein and biofuels: from strain selection to otdoor cultivation in a Green Wall Panel photobioreactor", Biotechnology for Biofuels, Biomed Central, Ltd, GB, (Jun. 7, 2014), vol. 8, No. 1, p. 84.

Ji, Y. et al. "Differential effects of phosphorus limitation on cellular metals in Chlore/la and Microcystis" Limnology and Oceanography, (Sep. 1, 2008), vol. 53, No. 5., pp. 1790-1804.

Krüger, "Kurze Charakteristik einiger niedrerer Organismen im Saftfluss der Laubbäume," Hedwigia, 33: 241-266, (1894). Machine Translation.

Miao et al., "High Yield Bio-Oil Production from Fast Pyrolysis by Metabolic Controlling of Chlorella Protothecoides," J. Biotech., 110:85-93, (2004).

Perez-Garcia, O. et al., "Heterotrophic cultures of microalgae: Metabolism and potential products", Water Research, Jan. 1, 2011, vol. 45, No. 1, pp. 11-36.

Pleissner, D. et a l. Effects of Phosphorous, Nitrogen, and Carbon Limitation on Biomass Composition in Batch and Continuous Flow Cultures of the Heterotrophic Dinoflagellate Crypthecodinium cohnil' Biotechnology and Bioengineering, Aug. 2012,pp. 205-2016, vol. 109, No. 8.

Qu, C.-B. et al. "Phosphate assimilation by Chlore/la and adjustment of phosphate concentration in basal medium for its cultivation" Biotechnology Letters, Oct. 20, 2008, pp. 1735-1740, vol. 30, No. 10.

Rhee, G-Yull, "Effects of N:P Atomic Ratios and Nitrate Limitation on Algal Growth, Cell Composition, and Nitrate Uptake", Limnology and Oceanography, vol. 23, No. 1 (Jan. 1978), pp. 10-25.

Sansawa et al., "Production of Intracellular Phytochemicals in Chlorella under Heterotrophic Conditions," Journal of Bioscience and Bioengineering, 98(6):437-444, (Jan. 1, 2004).

(56) References Cited

OTHER PUBLICATIONS

Shi et al., "Production and rapid extraction of lutein and the other lipid-soluble pigments from Chlorella protothecoides grown under heterotrophic and mixotrophic conditions," Nahrung, 43:109-113, (1999).

Shi, et al., "Production of biomass and lutein by Chlorella protothecoides at various glucose concentrations in heterotrophic cultures ," Process Biochemistry, 34:341-347, (1999).

Shi, X. M. et al., "High-Yield Production of Lutein by the Green Microalga Chlorella protothecoides in Heterotrophic Fed-Batch Culture," Biotechnol. Prog., 18(4):723-727 (2002).

Shihira-Ishikawa et al., "Nutritional Control of Cell Pigmentation In Chlorella Protothecoides With Special Reference to The Degeneration of Chloroplast Induced by Glucose," Plant and Cell Physiology, 5(2):227-240 (Feb. 1, 1964), [online abstract], Retrieved on Jun. 3, 2010 from http://pcp.oxfordjounals.org/cgi/content/abstract/5/2/227.

Syrett, P.J., "The Assimilation of Ammonia by Nitrogen-Strayed Celled of Chlorella vulgaris. Part II: The Assimilation of Ammonia to other Compounds", Annals of Botany, Academic Press, London, GB, (Jan. 1, 1953), vol. 17, No. 1, pp. 21-36.

Wu et al., "New Discoveries in Study on Hydrocarbons From Thermal Degradation of Heterotrophically Yellowing Algae," Science In China, 37(3):326-35, (Mar. 1, 1994).

Memorandum Order, Roquette Frères, S.A. v. Solazyme, Inc., C.A. No. 14-1442-SLR, District Court for the District of Delaware, Jan. 12, 2016.

Plaintiff and Counter-Defendant Roquette Frères, S.A.'s Reply Brief in Support of Its Motion for Stay Pending Appeal, Roquette Frères, S.A. v. Solazyme, Inc., C.A. No. 14-1442-SLR, District Court for the District of Delaware, Jan. 8, 2016.

Defendant and Counterclaimant Solazyme, Inc.'s Brief in Opposition to Plaintiff and Counter-Defendant Roquette Frères, S.A.'s Motion to Stay Pending Appeal, Roquette Frères, S.A. v. Solazyme, Inc., C.A. No. 14-1442-SLR, District Court for the District of Delaware, Jan. 6, 2016.

Declaration of Jonathan Wolfson in Support of Defendant and Counterclaimant Solazyme, Inc.'s Opposition to Plaintiff and Counterclaimant Roquette Frères, S.A.'s Motion to Stay Pending Appeal, Roquette Frères, S.A. v. Solazyme, Inc., C.A. No. 14-1442-SLR, District Court for the District of Delaware, Jan. 6, 2016, Redacted Public Version.

Declaration of Jeffrey M. Goehring in Support of Plaintiff and Counter-Defendant Roquette Frères, S.A.'s Brief Motion for Stay Pending Appeal, Roquette Frères, S.A. v. Solazyme, Inc., C.A. No. 14-1442-SLR, District Court for the District of Delaware, Dec. 28, 2015, Redacted Version • Exhibit 1, BASF and Solazyme Launch the First Commercial Microalgae-Derived Betaine Surfactant, Solazyme, Inc., Jul. 28, 2015 • Exhibit 2, Solazyme Bunge Renewable Oils Completes Key Redundant Power and Steam Supplies, Solazyme Bunge Renewable Oils, Jun. 30, 2015 • Exhibit 3, Solazyme Receives FDA GRAS No Questions Letter for High Oleic Algae Oil, Solazyme, Inc., Feb. 24, 2015 • Exhibit 4, Solazyme's (SZYM) CEO Jonathan Wolfson on Q1 2015 Results—Earnings Call Transcript, Solazyme, Inc., May 6, 2015 • Exhibit 5, Solazyme's (SZYM) CEO Jonathan Wolfson on Q2 2015 Results—Earnings Call Transcript, Solazyme, Inc., Jul. 30, 2015 • Exhibit 6, Solazyme's (SZYM) CEO Jonathan Wolfson on Q4 2014 Results—Earnings Call Transcript, Solazyme, Feb. 26, 2015 • Exhibit 7, Redacted In Its Entirety.

Motion to Stay Pending Appeal and Order Granting Motion to Stay Pending Appeal, Roquette Frères, S.A. v. Solazyme, Inc., C.A. No. 14-1442-SLR, District Court for the District of Delaware, Dec. 28, 2015.

Memorandum of Law in Support of Motion by Roquette Frères, S.A. for a Stay Pending Appeal, Roquette Frères, S.A. v. Solazyme, Inc., C.A. No. 14-1442-SLR, District Court for the District of Delaware, Dec. 28, 2015.

Email dated Nov. 3, 2015, from Gerald Suh of Solazyme, Inc., to Jeffrey M. Goehring of Young & Thompson International Patent & Trademark Law (counsel for Roquette Frères, S.A.).

Letter dated Oct. 6, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC), which included the following enclosures: • Exhibits 1, 9-12, and 14-15 to the Declaration of Jeffrey M. Goehring in Support of Roquette Frères, S.A.'s Brief in Support of Its Motion for Summary Judgment of Solazyme, Inc.'s Claim for Misappropriation of Trade Secrets, Roquette Frères, S.A. v. Solazyme, Inc., C.A. No. 14-01442, District Court for the District of Delaware, D.I. 141, Jun. 22, 2015, Redacted Version • Exhibits 2-8 to the Declaration of Jeffrey M. Goehring in Support of Roquette Frères, S.A.'s Brief in Support of Its Motion for Summary Judgment of Solazyme, Inc.'s Claim for Misappropriation of Trade Secrets, Roquette Frères, S.A. v. Solazyme, Inc., C.A. No. 14-01442, District Court for the District of Delaware, D.I. 112-1, Jun. 22, 2015 • Exhibit 13 to the Declaration of Jeffrey M. Goehring in Support of Roquette Frères, S.A.'s Brief in Support of Its Motion for Summary Judgment of Solazyme, Inc.'s Claim for Misappropriation of Trade Secrets, Roquette Frères, S.A. v. Solazyme, Inc., C.A. No. 14-01442, District Court for the District of Delaware, D.I. 112-2, Jun. 22, 2015 • Declaration of Jeffrey M. Goehring in Support of Roquette Frères, S.A.'s Brief in Support of Its Motion for Summary Judgment of Solazyme, Inc.'s Claim for Misappropriation of Trade Secrets, Roquette Frères, S.A. v. Solazyme, Inc., C.A. No. 14-01442, District Court for the District of Delaware, D.I. 112, Jun. 22, 2015 • Roquette Frères, S.A.'s Opening Brief in Support of Its Motion for Summary Judgment of Solazyme, Inc.'s Claim for Misappropriation of Trade Secrets, Roquette Frères, S.A. v. Solazyme, Inc., C.A. No. 14-01442, District Court for the District of Delaware, D.I. 140, Jun. 22, 2015, Redacted Version.

Letter dated Nov. 2, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC), which included the same enclosures included with the letter dated Oct. 6, 2015 of Cite No. CB.

Email dated Nov. 4, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC).

Opinion dated Dec. 21, 2015 in Roquette Frères, S.A., v. Solazyme, Inc., Case No. 1:14-cv-01442 (D. Del. 2015) granting Solazyme's motion for an order confirming the arbitration award rendered by CPR International Institute for Conflict Prevention & Resolution on Feb. 19, 2015, in favor of Solazyme, Inc.

"Auxenochlorella", article from Wikipedia, Retrieved from the Internet on Mar. 23, 2016, "https://en.wikipedia.org/w/index.php?title=Auxenochlorella&oldid=711518993".

Clore, G.M. And E.M. Chance, A computer analysis of cyanide stimulated oxygen uptake in Chlorella protothecoides. (Jul. 1977) FEBS Lett. 79 (2):353-356.

"Aoko's toxin", Aichi Prefectural Institute of Public Health, 6 pages. [Retrieved from the Internet Oct. 13, 2016: <URL: http://www.pref.aichi.jp/eiseiken/5f/bloom_t.html].

Lee, Yuan-Kun, "Commercial Production of microalgae in the Asia-Pacific rim", Journal of Applied Phycology, 9:403-411, (Oct. 29, 1997).

Kay, Robert A., "Microalgae as Food and Supplement", Critical Reviews in Food Sciense and Nutrition, 30(6):555-573 (Feb. 1991).

Usuki, Riichiro and Luniko Kamata,"Experimental Trials on the Role of Lipids in Good Taste and Good Body of Foods", Research reports of Shokei Gakuin College 53, May 2006, p. 85-90 (in Japanese with English Abstract).

"Chlorella Photosynthesis—Disctionary", last modified Mar. 23, 2015, Retrevied from the Internet: <URL: (http://photosyn.jp/pwiki/

(56) References Cited

OTHER PUBLICATIONS index.php?%E3%82%AF%E3%83%AD%E3%83%AC%E3%83%A9) with English Machine Translation.

Hirashima, Ryuta, "Framework of evaluation on inventive step requirement and significance of 'technical problem'", Patent 2010, 63(5): 34-49 (no translation).

Ullmann, Jorg, "The Difference between *Chlorella* vulgaris and *Chlorella* pyrenoidosa", (2006) (http://www.algomed.de/index.php?op=algenfarm_geschichte).

"History of the algae farm: Chlorella Algae—Roquette Klötze GmbH", [Retrieved from the Internet Nov. 25, 2016: <URL: (http://www.algomed.de/index.php?op=algenfarm_geschichte)].

Kirk, J. et al., "Mastitis Control Program for Prototheca Mastitis in Dairy Cows", 6 pages. <<URL: milkquality.wisc.edu/wp=content/uploads/2011/09/mastitis-control-program_prototheca-mastitis.pdf>>.

Oral Summary, dated Nov. 7, 2016, for Invalidation Hearing for Japanese Patent No. 5731982 (in Chinese).

Oral Summary by the Patentee, dated Nov. 29, 2016, for Invalidation Hearing for Japanese Patent No. 5731982 (in Chinese).

USDA National Nutriet Database (https://ndb.nal.usda.gov/ndb/).

Letter from Ray Matulka to Paulette Gaynor and Sylvester Mosley, dated Apr. 18, 2013, re: Request to Cease Evaluation of GRN 000450, Letter from Ray Matulka to Paulette Gaynor, dated Apr. 18, 2013, re: High Lipid Chlorella protothecoides S106 Flour GRAS Notification and GRAS Exemption Claim (dated Apr. 18, 2013).

Solazyme Market and Products, (2005).

Letter from Susan Cho to Susan Carlson, dated Jul. 25, 2011 and "RF1's Chlorella vulgaris GRAS Self affirmation (dated Jul. 16, 2010)."

"Roquestte Freres, S.A. and Solazyme, Inc. Agree to Dissolve Microalgae Join Venture", (Jun. 24, 2013) Press Release, Lestrem, France.

Standard Tables of Food Composition in Japan 2015 (Seventh Revised Edition), Table of Fatty Acid Composition, Edited by the Council for Science and Technology, the Ministry of Education, Culture, Sports, Science and Technology, (available from http://www.mext.gojp/a_menu/syokuhinseibun/1365295.htm) [Retrieved from the Internet Oct. 12, 2016: <URL: (http://www.algomed.de/index.php?op=algenfarm_geschichte)]http://www.geocities.jp/jr2bvb/syokuhin/sibousan/oil_s.htm].

"'Taste' of Lipids?" [Retrieved from the Internet Oct. 12, 2016: <URL: (https://sites.google.com/site/coffeetambe/coffeescience/physiology/taste/fat] with English Machine Translation.

Japanese Laid-Open Publication No. 2000-175680 (translator's note: an English language member of the same patent family: EP 1142985 (A1)).

Japanese Laid-Open Publication No. 2002-223787 (translator's note: no English language counterpart could be located).

http://mcc.nies.go.jp/strainList.do?strainId=2555&condition=Auxenochlorella+protothecoides.

http://mcc.nies.go.jp/strainList.do?strainId=2568&condition=Auxenochlorella+protothecoides.

*Roquette Freres S.A. v. Solazyme Inc.*, Delaware District Court, Case No. 1:14-cv-01442 District Judge Sue L. Robinson, presiding, Solazyme, Inc.'s Answer to Plantiff Roquette Freres, S.A.'s Complaint, Petition to Confirm Arbitration Award and Counterclaims, filed Feb. 26, 2015, 29 pages.

Joint Venture and Operating agreement of Solazyme Roquette Nutritionals, LLC., dated Nov. 7, 2015.

*Solazyme, Inc.* vs. *Roquette Freres, S.A.*, Arbitration Award, dated Feb. 19, 2015.

Request for Invalidation, dated Jan. 7, 2015, for Chinese Patent Application No. 200980149978.1, 21 pages (in Chinese).

Supplemental Statement for Request for Invalidation, dated Dec. 2, 2015, for Chinese Patent Application No. 200980149978.1, 35 pages (in Chinese), including the list of submitted Counter Evidences on p. 1-2.

Notification of Acceptance of Request for Invalidation, dated Jan. 28, 2016, for Chinese Patent Application No. 200980149978.1, 4 pages (in Chinese).

Documents filed by the Petitioner—Part II, dated Apr. 29, 2015, for Chinese Patent Application No. 200980149978.1, 21 pages (in Chinese), including : • Jia, Xuan, et al., "Removal of Total nitrogen form wastewater dischrage from a chemical pertilizer plant by Chlorella protothecoides USTB-01", Chinese Journal of Environmental Engineering, (Apr. 2010), 4(4):737-740 (in Chinese).

Documents filed by the Petitioner—Part III, dated May 5, 2015, for Chinese Patent Application No. 200980149978.1, 21 pages (in Chinese), including : , including : • Singelton Paul and Diana Sainsbury, "Dictionary of Microbiological and Molecular Biology, (3rd Ed. 2006)", pp. 155 (and Chinese translation thereof) • Singelton Paul and Diana Sainsbury, "Dictionary of Microbiological and Molecular Biology, (2nd Ed. 1987)", pp. 178-179 (and Chinese translation therof).

Statement of Grounds & Particulars of Opposition, Grounds for Opposition, In the matter of Australian Patent Application No. 2009303354 in the name of Solazyme, Inc. and Opposition by *Roquette Frères, S.A.* v. *Solazyme, Inc.*, Commonwealth of Australia, Mar. 3, 2016, (21 pages).

Declaration of Michael Armin Borowitzka In the matter of Australian Patent Application No. 2009303354 in the name of Solazyme, Inc. and Opposition by *Roquette Frères, S.A.* v. *Solazyme, Inc.*, Commonwealth of Australia, Jun. 2, 2016, (32 pages).

• Exhibit MB-1, Federal Court of Australia, Practice Note CM7, Expert Witnesses in Proceedings on the Federal Court of Australia, commenes Jun. 4, 2013 • Exhibit MB-2, Michael Armin Borowitzka Curriculum Vitae Exhibit • MB-3, J. M. Hundley, R. B. Ing and R. W. Krauss, "Algae as Sources of Lysine and Threonine in Supplementing Wheat and Bread Diets", Science, New Series, vol. 124, No. 3221 (Sep. 21, 1956), pp. 536-537. • Exhibit MB-4, Krauss, Robert W., "Mass Culture of Algae for Food and Other Organic Compounds," American Journal of Botany, vol. 49, No. 4 (Apr. 1962), pp. 425-435. • Exhibit MB-5, Lee, Yuan-Kun, "Commercial Production of microalgae in the Asia-Pacific rim", Journal of Applied Phycology, 9:403-411, (Oct. 29, 1997) • Exhibit MB-6, Soong, Pinnan, "Productions and Development of *Chlorella* and *Spirulina* in Taiwan", *Algae Biomass: Production and Use,* Gedaliah Shelef and Carl J. Soeder (eds.), North-Holland Biomedical Press, (Dec. 1980), pp. 97-113 and title and copyright page. • Exhibit MB-7, Kawaguchi, Kotaro, "Microalgae Production Systems in Asia", *Algae Biomass: Production and Use,* Gedaliah Shelef and Carl J. Soeder (eds.), North-Holland Biomedical Press, (Dec. 1980), pp. 25-33 and title and copyright page. • Exhibit MB-8, Kay, Robert A., "Microalgae as Food and Supplement", Critical Reviews in Food Science and Nutrition, 30(6):555-573 (Feb. 1991). • Exhibit MB-9, Raymundo et al., "Fat mimetic capacity of Chlorella vulgaris biomass in oil-in-water food emulsions stabilized by pea protein," Food Research International, 38:961-965, (Feb. 25, 2005). • Exhibit MB-10, Samejima, H. and J Myers, "On the Heterotrophic Growth of Chlorella *pyrenoidosa*", J. Gen Microbiol, (1958), 18: 107-117. • Exhibit MB-11, Aoki, Shigeji and Eiji Hase, "De- and Re-Generation of Chloroplasts in the Cells of Chlorella Protothecoides", Plant & Cell Physiol, (Sep. 5, 1964), vol. 5, pp. 473-484 [Retrieved from the internet on Jun. 7, 2013 from http://pcp.oxfordjournals.org/ by Reprints Desk ]. • Exhibit MB-12, Becker, E.W., "Micro-algae as a source of protein," Biotechnology Advances, 25:207-201, (Mar.-Apr. 2007). • Exhibit MB-13, Iwamoto, Hiroaki, "Industrial Production of Microalgal Cell-mass and Secondary Products—Major Industrial Species Chlorella", Chapter 11, Handbook of Microalgal Culture: Biotechnology and Applied Phycology, Amos Richmond (eds), (Dec. 1, 2003), pp. 255-263. • Exhibit MB-14, Petkov et al., "Which are fatty acids of the green alga Chlorella?," Biochemical Systematics and Ecology, 35:281-285, (2007). • Exhibit MB-15, Gladu, Patricia K., et al. "Sterol, Fatty Acid and Pigment Characteristics of UTEX 2341, a Marine Eustigmatophyte Identified Preivously as Chlorella Minutissuma (Chlorophyceae)" J. Phycol., (Jun. 21, 1995), 31:774-777. • Exhibit MB-16, Xu et al., "High Quality Biodiesel Production From a Microalga Chlorella Protothecoides by Heterotrophic Growth In Fermenters," Journal of Biotechnology, 126(4):499-507, (May 2006). • Exhibit MB-17, Matsuka et al.,

(56) References Cited

OTHER PUBLICATIONS

"Changes in Contents of Carbohydrate and Fatty Acid in the Cells of Chlorella Protothecoidesduring the process of De- and Re-Generation of Chloroplasts," Plant and Cell Physiol., 7:651-662 (Sep. 24, 1966). • Exhibit MB-18, Xuan, J. et al., "Removal of total nitrogen from wastewater discharge from a chemical fertilizer plant by Chlorela protothecoides USTB-01", Chinese Journal of Environmental Engineering, (Apr. 2010), vol. 4, No. 4, pp. 737-740.
• Exhibit MB-19, Australian Application No. 2009303354B2 from International Patent Application No. PCT/US2009/060692, naming Solazyme, Inc., International Patent Publication No. 2010/045368, dated Apr. 22, 2010. • Exhibit MB-20, Pabst, W., "Nutritional evaluation of nonsewage microalgae by the rat balance method," Arch. HyrobioL Beih, (Dec. 1978), pp. 65-70 • Exhibit MB-21, Urano, et al., "Effect of Osmotic Stabilizers on Protoplast Generation on Chlorella ellipsoidea Yellow/White Color Mutants", Journal of Bioscience and Bioengineering, vol. 90, No. 5, 567-569, (2000).
• Exhibit MB-22, Kamiya, "Effects of Blue Light and Ammonia on Nitrogen Metabolism in a Colorless Mutant of Chlorella", Plant Cell Phyiol., 30(4):513-521 (1989) • Exhibit MB-23, Biello et al., "Biofuel of the Future: Oil from Algae," Scientific American, 2 pages, (Jan. 9, 2008).
Evidence in Support, In the matter of Australian Patent Application No. 2009303354 in the name of Solazyme, Inc. and Opposition by *Roquette Frères, S.A.* v. *Solazyme, Inc.*, Commonwealth of Australia, Jun. 3, 2016, (1 page).
Declaration of Young J. Suh In the matter of Australian Patent Application No. 2009303354 in the name of Solazyme, Inc. and Opposition by *Roquette Frères, S.A.* v. *Solazyme, Inc.*, Commonwealth of Australia, Aug. 31, 2016, (94 pages) • Exhibit YS1, Arbitration Award, *Solazyme Inc.* vs. *Roquette Frères,* Case 1:14-cv-01442-SLR, Document 153, Filed Dec. 21, 2015 • Exhibit YS2, French Patent Publication No. FR 2 924 126, filed Nov. 28, 2007.
• Exhibit YS3, Memorandum Opinion, Document 153, *Roquette Frères, S.A.* vs. *Solazyme Inc.,* Case 1:14-cv-01442-SLR, filed Dec. 21, 2015.
Declaration of Craig Patch In the matter of Australian Patent Application No. 2009303354 in the name of Solazyme, Inc. and Opposition by *Roquette Frères, S.A.* v. *Solazyme, Inc.*, Commonwealth of Australia, Sep. 5, 2016, (22 pages) • Exhibit CP-1, Federal Court of Australia, Practice Note CM7, Expert Witnesses in Proceedings on the Federal Court of Australia, commenes Jun. 4, 2013.
• Exhibit CP-2, Craig Patch Curriculum Vitae.
Declaration of Craig Patch In the matter of Australian Patent Application No. 2009303354 in the name of Solazyme, Inc. and Opposition by *Roquette Frères, S.A.* v. *Solazyme, Inc.*, Commonwealth of Australia, Sep. 28, 2016, (42 pages). • Exhibit CP3, Record of Views Formed in Response to Inquires, updated Mar. 2015 (20 pages) • Exhibit CP4, Huss, V.A.R., et al., "Biochemical Taxonomy and Molecular Phylogeny of the Genus *Chlorella Sensu Lato* (Chlorophyta)1", J. Phycol. 35, 587-598 (Jan. 15, 1999).
Evidence in Answer, In the matter of Australian Patent Application No. 2009303354 in the name of Solazyme, Inc. and Opposition by *Roquette Frères, S.A.* v. *Solazyme, Inc.,* Commonwealth of Australia, Sep. 29, 2016, (1 page).
Declaration of Michael Armin Borowitzka In the matter of Australian Patent Application No. 2009303354 in the name of Solazyme, Inc. and Opposition by *Roquette Frères, S.A.* v. *Solazyme, Inc.,* Commonwealth of Australia, Dec. 21, 2016, (14 pages).
Evidence in Reply, In the matter of Australian Patent Application No. 2009303354 in the name of Solazyme, Inc. and Opposition by *Roquette Frères, S.A.* v. *Solazyme, Inc.,* Commonwealth of Australia, Dec. 23, 2016, (1 page).
"Roquette's Microalgae High Lipid Algal Flour Wins Most Innovative Food Ingredient at the 2013 Fi Europe Excellence Award," www.PRnewswire.com/news-release/roquettes-migroalgae-high-lipid-algal-flour-wins-most-innovative-food-ingrediant-at-the-2013-fi-europe-excellence-awards, (Nov. 25, 2013), pp. 1-5.

Freshwater Algae Culture Collection at the Institute of Hydrobiology (FACHB-collection), certification letter by the Chinse Academy of Science, "Chlorella vulgaris", (No Date).
Zhou, Lian-ning et al. "Effects of Environmental Factors on Nitrogen and Phosphorus Removal by *Chlorella vularis* in Wastewater", Current Biotechnology, (Jan. 25, 2015), vol. 5, No. 1, Title page, Publication Page, Table of Contents (I Chinese and English), pp. 60-65, with English abstract.
Evidence 1, Explanation paper, filed with IP High Court Case No. H29 (gyo-ke) 10149 on Oct. 6, 2017 in Invalidation Appeal No. 2016-800012 against Japanese Patent No. 5731982, with English translation.
First Statement, Substantive Brief, filed with IP High Court Case No. H29 (gyo-ke) 10149 on Nov. 17 2017 in Invalidation Appeal No. 2016-800012 against Japanese Patent No. 5731982, with English translation.
Second Statement, Substantive Brief, filed with IP High Court Case No. H29 (gyo-ke) 10149 on Jan. 17, 2018 in Invalidation Appeal No. 2016-800012 against Japanese Patent No. 5731982. With Explanation Paper for the Evidence. Japanese Only.
Opponent's Outline of Submissions, in the Matter of Australian Patent Application No. 2009303354 in the name of Corbion Biotech, Inc., dated Jan. 24, 2018, 48 pages.
Response to Reg 5.23 Request, in the Matter of Australian Patent Application No. 2009303354 in the name of Corbion Biotech, Inc., filed Feb. 5, 2018, 18 pages. • Letter from David Sieveking, dated Jan. 24, 2018 • Statutory Declaration of Dr Daniel Peter Sieveking, dated Jan. 24, 2018. • Exhibit DS-1, Kyle, David, "Production and Use of Lipids from Microalgae", Microalgal Lipids, Lipid Technology, (May-Jun. 1992), pp. 59-64. • Exhibit DK-2, Chen et al., "High cell density culture of microalgae in heterotrophic growth," Trends In Biotechnology, 14:421-426, (1996).
Consent to Withdraw, dated Feb. 14, 2018, for IP High Court Case No. H29 (gyo-ke) 10149, Invalidation Appeal No. 2016-800012, against Japanese Patent No. 5,731,982, in the names of TerraVia Holdings, Inc. in Japanese Only, [SOLAO043JP-0807X01JP].
Request for Withdrawal of Opposition, by Roquette Freres, to Grant of Australian Patent Application No. 2009303354, in the Name of Corbion Biotech, Inc., dated Mar. 13, 2018.
Opposition Proceedings, dated Mar. 14, 2018, Acknowledgement of the the Request for Withdrawal of Opposition, by Roquette Freres, to Grant of Australian Patent Application No. 2009303354.
U.S. Appl. No. 15/953,312, filed Apr. 13, 2018, Gabriel Macquart.
U.S. Appl. No. 15/698,579, filed Sep. 7, 2017, Brooks et al.
European Patent Application No. EP 14 789 311.9, First Examination Report, dated Oct. 10, 2017. (in French).
Japanese Patent Application No. JP 2016-535517, English Translation of the Notice of Reasons for Rejection, dated May 21, 2018.
European Patent Application No. EP 14 789 311.9, Second Office Action, dated Jul. 19, 2018. (in French).
Chinese Patent Application No. 201480046493.0, Rejection Decision, dated Sep. 18, 2018.
Chen et al., (1991) "Effect of C/N ratio and aeration on the fatty acid composition of heterotrophic *Chlorella sorokiniana,"* Journal of Applied Phycology, 3:203-209.
Miao et al., "Biodiesel Production From Heterotrophic Microalgal Oil," Biosource Technology, 97(06):841-846, (2006).
Samarasinghe, Nalin, et al., "Algal Cell Rupture Using High Pressure Homogenization as a Prelude to Oil Extraction." Renewable Energy, vol. 48, (Apr. 20, 2012) pp. 300-308, 2012.
Wu et al., "A Comparative Study of Gases Generated from Simulant Thermal Degradation of Autotrophic and Heterotrophic Chlorella," Progress in Natural Science, 2(4):311-318, (1992).
Wu et al., "Comparative study on Liposoluble Compounds in Autotrophic and Heterotrophic Chlorella Protothecoides," Acta Botanica Sinica, 35(11):849-858, (1992).
Youzhi Jiagong, (Jun. 8, 2007), "Oil Processing Technology (2nd edition)", Chemical Industry Press, Title page, Publication page, Table of Contents, pp. 206-213, (in Chinese).
"Linoleic acid and α-linolenic acid are real essential fatty acids", (Mar. 1998), Title page, Publication Page, Table of Contents,

(56) References Cited

OTHER PUBLICATIONS

Chapter 2: Essential Fatty Acids (pp. 12-13) and Chapter 15: Selection of the most suitable fatty acids (pp. 89-91), with English translation.
Bowman, Barbara A. and Robert M. Russell (eds.), "Present Knowledge in Nutrition" (1st Edition), (Oct. 2004), Title page, Publication Page, Table of Contents, p. 231 (in Chinese).
"Algen—Nudein ais Altmark Spezialitat (Algae noodles: a speciality from Altmark region)" in German language, and other *Chlorella* Food products, (Oct. 9, 2007), 3 pages.
Imai, Ichiro, et al. "Advanced research on Shellfish poisonings: Current Status and overview", (Mar. 20, 2007), Table of Contents, Chapters 1 and Chapter 4, 11 pages.
Environmental Stresses in Non Mammalian Organisms, p. 29. with English translation.
[Retrieved from the Internet Oct. 13, 2016: <URL: http://hfnet.nih.go.jp/contents/detail105.htm] (in Chinese).
Third Party Observations from Roquette Freres, dated Aug. 31, 2017, for Chinese patent for invention No. 200980149978.1 (in Japanese with English Translation).
Third Party Observations from Roquette Freres, dated Aug. 31, 2017, for Chinese patent for invention No. 201080026237.7 (in Japanese with English Translation).

\* cited by examiner

METHOD FOR THE INDUSTRIAL PRODUCTION OF FLOUR FROM LIPID-RICH MICROALGA BIOMASS WITH NO "OFF-NOTES" BY CONTROLLING THE OXYGEN AVAILABILITY

CROSS-REFERENCE TO RELATED APPLICATION

This application is the U.S. national stage application of International Patent Application No. PCT/FR2014/052113, filed Aug. 22, 2014.

The present invention relates to a novel process for the production, on an industrial scale, of biomass of lipid-rich microalgae of the *Chlorella* genus of acceptable sensory quality.

The present invention is particularly suitable for controlling the oxidative rancidity which accompanies the instability over time of biomass of microalgae rich in monounsaturated fatty acids, in particular in oleic acid.

PRESENTATION OF THE PRIOR ART

Historically requiring "only water and sunlight" to grow, algae have for a long time been considered to be a source of food.

There are several species of algae that can be used in food, most being "macroalgae" such as kelp, sea lettuce (*Ulva lactuca*) and red algae of the type *Porphyra* (cultured in Japan) or "dulse" (*Palmaria palmata*).

However, in addition to these microalgae, there are also other algal sources represented by the "microalgae", i.e. photosynthetic or non-photosynthetic single-cell microscopic algae, of marine or non-marine origin, cultured for their applications in biofuels or food.

For example, spirulin (*Arthrospira platensis*) is cultured in open lagoons (under phototrophic conditions) for use as a food supplement or incorporated in small amounts into confectionery products or drinks (generally less than 0.5% weight/weight).

Other lipid-rich microalgae, including certain species belonging to the *Chlorella* genus, are also very popular in Asian countries as food supplements.

Several species of microalgae are capable of changing from photoautotrophic growth (growth by virtue of light, which supplies the energy for converting $CO_2$ into carbon-based chains) to heterotrophic growth (without light) using glucose or other carbon-based substrates which can be used for the metabolism of carbon and energy.

Three processes for the production of microalgae are currently used industrially:
  in heterotrophic reactors (entirely closed);
  in open-air ponds;
  in glass tubes.

Chlorellae with variable properties and compositions are produced from these methods of culturing. Their composition will be different according to whether or not they are produced in light and whether or not they are produced in the open air.

The production and the use of flour of microalgae of *Chlorella* type are, for example, described in documents WO 2010/120923 and WO 2010/045368, the production via the heterotrophic route and in the absence of light promoting their growth rate.

The oil fraction of the microalgal flour, which can be composed essentially of monounsaturated oils, can offer nutritional and health advantages in comparison with the saturated, hydrogenated and polyunsaturated oils often found in conventional food products.

However, when it is desired to industrially manufacture microalgal flour powders from their biomass, major difficulties remain, not only from the technological viewpoint, but also from the viewpoint of the sensory profile of the compositions produced.

Indeed, while algal powders, for example manufactured with algae photosynthetically cultured in outside ponds or by photobioreactors, are commercially available, they have a dark green color (associated with chlorophyll) and a strong unpleasant taste.

Even formulated in food products or as nutritional supplements, these algal powders always give the food product or the nutritional supplement this visually unattractive green color and have an unpleasant fishy taste or the savor of marine algae.

As for Chlorellae, the descriptor commonly accepted in this field is the taste of "green tea", slightly similar to other green vegetable powders such as powdered green barley or powdered green wheat, the taste being attributed to its high chlorophyll content.

Their savor is usually masked only when they are mixed with vegetables with a strong savor or citrus fruit juices.

Moreover, for lipid-rich Chlorellae, unpleasant savors (off-notes) can occur, associated in particular with the products of oxidative degradation of lipids, especially that of monounsaturated fatty acids.

Thus, for example, oleic acid (C18:1) is sensitive to oxidation, and its oxidative degradation results in:
  the formation of peroxides, of hydroperoxides and of volatile organic compounds with a rancid odor, and
  the loss of the nutritional value of unsaturated fatty acids.

The products of oxidative degradation (enzymatic or by auto-oxidation) of unsaturated fatty acids are mainly carbonyl compounds and alcohols composed of 5 to 9 carbons which confer very specific odors.

Thus, the compounds comprising 9 carbons, such as (E,Z)-2,6-nonadienal, have cucumber and melon odors. The compounds comprising 8 carbons (1-octen-3-ol, 1-octen-3-one, 1,5-octadien-3-ol) contribute to the odor of plants or to the metallic odor, even though individually these compounds have mushroom or geranium odors. The compounds comprising 6 carbons (hexanol, hexanal, (H)-2-hexenal and (Z)-3-hexen-1-ol) participate in the green odor and in the odor of algae. (E,E)-2,4-heptadienal has, for its part, a green odor, of cucumber.

In order to control the oxidative degradation of fatty acids on a laboratory scale, the degree of aeration of the biomass in order to meet the oxygen needs of the microalga is controlled by monitoring the dissolved oxygen pressure ($pO_2$).

The fermentation protocol then comprises a regulation of the $pO_2$ carried out by means of:
  the air flow rate and/or
  the oxygen flow rate and/or
  the stirring power.

However, this control of the $pO_2$ poses great difficulties when it is a question of transposing the protocol from the laboratory to the industrial scale.

This is because the $pO_2$ is defined according to the dissolved oxygen concentration in the fermentation must at saturation. If water is aerated under air, at ambient temperature and under atmospheric pressure, for a sufficiently long period of time, it is considered that the $pO_2$ is equal to 100%.

In point of fact, during the calibration of a $pO_2$ probe in a fermenter, the dissolved oxygen content is influenced by the concentration of residual salts and by the fermentation temperature.

Moreover, it is conventionally accepted that, for a laboratory fermenter, the $pO_2$ is barely influenced by the pressure generated by the height of the fermentation must and by the mixing effects.

However, during industrializations on fermenters of medium (about 1 $m^3$) to large capacity (about a few hundred $m^3$), the height of the fermentation must will, on the contrary:

have an influence on the dissolved oxygen pressure; and
cause complex phenomena in the "not perfectly stirred" fermenter.

In this sense, the $pO_2$ value established on a laboratory scale cannot therefore be extrapolated to an industrial scale.

There is therefore still an unsatisfied need to have a process which guarantees the industrial-scale production of compositions of flour of microalgae of the *Chlorella* genus of suitable organoleptic quality enabling the use thereof in a greater number of more diversified food products.

SUMMARY OF THE INVENTION

The applicant company has found that it is possible to overcome this difficulty in controlling the availability of dissolved oxygen which must be sufficient to meet the needs of the microalga while at the same time preventing as much as possible the oxidative degradation of the monounsaturated fatty acids produced, by adjusting said oxygen transfer needs by monitoring the respiratory quotient (using a gas analyzer), and not by monitoring the response of a $pO_2$ probe.

This control makes it possible, moreover:
to visualize the metabolic behavior of the strain and
to overcome the problems of overoxygenation which can only be observed conventionally by measuring the $pO_2$.

Thus, the present invention relates to a process for the fermentative production of a biomass, preferably on an industrial scale, of lipid-rich microalgae, comprising at least one culturing step during which the dissolved oxygen availability in the fermenter is controlled by monitoring the respiratory quotient of said microalgae.

The microalgae are preferably cultured under heterotrophic conditions.

The microalgae preferably belong to the *Chlorella* genus and can be chosen from the group consisting of *Chlorella vulgaris*, *Chlorella sorokiniana* and *Chlorella protothecoides*. Quite particularly preferably, the microalgae are *Chlorella protothecoides*.

The microalgae are lipid-rich. The biomass obtained can in particular have a lipid content of more than 30% or 40% by dry weight of biomass.

The culturing step during which the dissolved oxygen availability in the fermenter is controlled by monitoring the respiratory quotient is preferably a lipid accumulation step. In particular, the dissolved oxygen availability in the fermenter can be controlled by monitoring the respiratory quotient as soon as the biomass has a lipid content of more than 25%, preferably more than 30% by dry weight of biomass.

The process according to the invention makes it possible to obtain a biomass of acceptable sensory quality, in particular comprising little or no organoleptically undesirable compounds such as the products of oxidative degradation of monounsaturated fatty acids, and more particularly the products of oxidative degradation of oleic acid. The evaluation of this sensory quality can be carried out in particular by means of descriptors comprising color, coating texture, sweetness, and the following flavors: mushroom, cereals, butter/dairy product, rancid oil and vegetable aftertaste.

The sensory analysis can be carried out using a microalgal flour composition comprising:
5-10% of microalgal flour composition, preferably approximately 7%;
0.5-2% of sugar, preferably approximately 1%;
0.1-0.5% of vanilla flavoring, preferably approximately 0.25%; and
the remainder being skimmed milk, preferably approximately 91.75%, the percentages being by weight of the composition, said composition being homogenized and heated at 60-85° C., preferably approximately 75° C., for 2-10 minutes, preferably approximately 5 minutes.

The sensory analysis can also comprise the analysis by SPME/GC-MS of the volatile organic compounds associated with the descriptors of the sensory analysis. Preferably, the volatile organic compounds belong to the families of saturated and diunsaturated aldehydes, unsaturated ketones, and carboxylic acids and derivatives thereof.

In order to prevent or reduce the production of these undesirable compounds, the respiratory quotient can be maintained, during the monitoring period, preferably during the lipid accumulation phase when the lipid content is more than 25% by dry weight of biomass, at a value greater than 1.5, preferably greater than 1.6, more preferentially greater than 1.7 and even more preferentially greater than 1.8.

The respiratory quotient can be monitored by means of a gas analyzer and can be controlled by supplying the fermentation medium with oxygen in particular by modulating the stirring speed, the backpressure or the oxygen concentration in the entering air (air injected into the medium).

This control also makes it possible to obtain a cumulative $YO_2/S$ metabolic ratio (calculated from the beginning of the fermentation) maintained at a value of less than 0.28, preferentially less than 0.27, more preferentially less than 0.26. Alternatively, it also makes it possible to obtain a $YO_2/S$ metabolic ratio observed during the lipid accumulation phase, preferably when the biomass contains more than 25% of lipids, preferably more than 30% of lipids (% expressed by dry weight of biomass), maintained at a value of less than 0.28, preferentially less than 0.27, more preferentially less than 0.26.

DETAILED DESCRIPTION OF THE INVENTION

Definitions

For the purposes of the invention, a microalgal flour composition has an "acceptable sensory quality" when its evaluation by a sensory panel in a food formulation concludes that there is an absence of off-notes which modify the organoleptic quality of said food formulations containing these microalgal flour compositions.

The "off-notes" are associated with the presence of specific undesirable odorous and/or aromatic molecules.

The term "organoleptic quality" is intended to mean the property of a food in terms of taste, odor, appearance, color and consistency.

The "respiratory quotient" corresponds to the ratio between the amount of $CO_2$ produced and the amount of $O_2$ consumed per unit of time. This quotient can be obtained by analyzing the gases leaving the fermenter.

The "$Y_{O2/S}$ metabolic ratio" corresponds to the ratio between the amount of $O_2$ consumed and the amount of substrate, generally glucose, consumed.

"The productivity" corresponds to the amount of biomass produced per liter and per hour of fermentation in fed-batch mode.

"The Yx/s conversion yield" conventionally represents the ratio between the biomass formed and glucose consumed.

"The microalgae of the *Chlorella* genus" is intended to mean herein microalgae chosen from the group consisting of *Chlorella protothecoides, Chlorella kessleri, Chlorella minutissima, Chlorella sp., Chlorella sorokiniana, Chlorella luteoviridis, Chlorella vulgaris, Chlorella reisiglii, Chlorella ellipsoidea, Chlorella saccarophila, Parachlorella kessleri, Parachlorella beijerinkii, Prototheca stagnora* and *Prototheca moriformis*, preferably chosen from the group consisting of *Chlorella vulgaris, Chlorella sorokiniana* and *Chlorella protothecoides*. Particularly preferably, the microalgae are *Chlorella protothecoides*.

Subject of the Invention

Those skilled in the art conventionally determine the dissolved oxygen availability in the fermentation medium by measuring the oxygen partial pressure ($pO_2$).

This technique is satisfactory on small fermenters since the value given by a $pO_2$ probe can be considered to be representative of the entire fermenter.

However, it does not make it possible to know the overall $O_2$ availability in a large industrial fermenter since the $pO_2$ is not uniformly distributed therein.

In order to overcome this problem, the applicant company has therefore developed a method for controlling the oxygenation by means of the level of the respiratory quotient of the fermentation, which is a rapid and reliable indicator of the metabolism of the microalgae contained in the fermenter.

The invention therefore relates to a novel process for the industrial production of biomass of microalgae, preferably of the *Chlorella* genus, rich in lipids and with no organoleptically undesirable compounds. This process is characterized by the controlling of the dissolved oxygen availability using an indirect method (monitoring of the respiratory quotient of the microalgal strain) suitable for large fermenters, the notion of indirect method contrasting with the direct method of measuring the dissolved oxygen availability by means of a probe which measures the oxygen partial pressure ($pO_2$).

The object of controlling the dissolved oxygen availability by monitoring the respiratory quotient of the microalga is to reduce the synthesis of molecules responsible for the appearance of off-notes (in particular the products of oxidative degradation of monounsaturated fatty acids such as oleic acid).

Indeed, the development of the metabolic pathways resulting in the undesirable molecules depends on the $O_2$ availability in the fermentation medium.

These degradation pathways demand more oxygen than the metabolic pathways for biosynthesis of the molecules of interest, in the case in point the metabolic pathways for biosynthesis of monounsaturated fatty acids of C18:1 oleic type.

This results in a lower respiratory quotient for these degradation pathways than for the biosynthesis pathway targeted.

Thus, as is illustrated in the examples, for *Chlorella protothecoides* chosen as reference microalga in the process of the invention, the respiratory quotient is 1.8—which reflects the production of 1.8 mol of $CO_2$ per mole of $O_2$ consumed—when the oleic acid biosynthesis pathway is predominant in the cell metabolism.

On the other hand, when the fermentation is over-oxygenated and the microalgae generate oxidative degradation products, the respiratory quotient does not exceed 1.5.

The process according to the invention is a process for the fermentative production of lipid-rich biomass, which comprises a culturing step during which the dissolved oxygen availability in the fermenter is controlled by monitoring the respiratory quotient of the microalgae.

The microalgae are preferentially of the *Chlorella* genus. In particular, they may be chosen from the group consisting of *Chlorella vulgaris, Chlorella sorokiniana* and *Chlorella protothecoides*. Preferably, the microalgae are *Chlorella protothecoides*.

Although it can be used on a smaller scale, the process is preferably carried out on an industrial scale, i.e. in fermenters of medium capacity (of approximately 1 to 100 $m^3$) and large capacity (of more than 100 $m^3$). According to one embodiment, the process is carried out in fermenters with a capacity of at least 1, 10, 25, 50, 75, 100, 500 or 1000 $m^3$.

According to one preferred mode, the microalgae are cultured under heterotrophic conditions, i.e. without light using a carbon-based substrate (preferably glucose) as carbon and energy source.

The biomass obtained by means of the process according to the invention is a lipid-rich biomass. The expression "lipid-rich" as used in the present application refers to a lipid content of more than 20% by dry weight of biomass, preferably of more than 25%. According to one particular embodiment, the biomass obtained by means of the process according to the invention has a lipid content of more than 30%, 35%, 40% or 44% by dry weight of biomass.

Preferably, the culturing step during which the dissolved oxygen availability in the fermenter is controlled by monitoring the respiratory quotient of the microalgae is the step during which the biomass accumulates lipids.

The lipid accumulation phase is the culture phase during which the fatty acid content of the biomass increases. This step may be subsequent to a growth step intended exclusively to increase the amount of biomass. It may be triggered when the amount of biomass has reached a predefined threshold, for example approximately 70 g/l, in particular by replacing the aqueous ammonia with potassium hydroxide in order to regulate the pH.

More particularly preferably, the dissolved oxygen availability in the fermenter is controlled by monitoring the respiratory quotient as soon as the fatty acid content is greater than 25% by dry weight of the biomass, preferably greater than 30% by dry weight of the biomass. Alternatively, the monitoring of the respiratory quotient of the microalgae can be carried out throughout the duration of the fermentation.

According to one preferred mode, the biomass obtained by means of the process according to the invention is of acceptable sensory quality. In particular, it contains little or no organoleptically undesirable compounds such as the products of oxidative degradation of monounsaturated fatty acids. In particular, the biomass contains little or no oleic acid oxidative degradation products.

Preferably, the content of organoleptically undesirable compounds remains below the detection threshold of a sensory panel. In particular, the content of linoleic acid (oleic acid oxidative degradation product) is less than 18%, 17%, 16%, 15%, 14%, 13%, 12%, 11%, 10%, 9%, 8% or 7% by weight relative to the total weight of the fatty acids in the dry biomass.

The sensory quality of the biomass can be defined by preparing a microalgal flour tasting composition and by asking a panel, preferably of at least 10 individuals, to evaluate descriptors relating to appearance, texture, savors and flavors.

The microalgal flour can be prepared from ground and dried biomass by any method known to those skilled in the art, such as for example the one described in patent application WO 2010/12093. The term "microalgal flour composition" is intended to mean a composition comprising at least 50%, 60%, 70%, 80%, 90% or 95% by dry weight of microalgal biomass. However, other ingredients may optionally be included in this composition. The microalgal biomass is derived from microalgal cells, which may be whole or broken, or a mixture of whole and broken cells.

The applicant company has moreover defined, in French patent application No. 13 56113, a very simple tasting matrix which makes it possible to perform an organoleptic evaluation similar to that obtained with much more complex and very different recipes such as an ice cream or a brioche. The evaluation with this tasting matrix is much more precise or accurate than that performed with a simple aqueous solution, which has proved to be incapable of predicting the organoleptic qualities of microalgal flour compositions in an ice cream, for example.

Thus, preferably, the microalgal flour tasting composition used to evaluate the sensory qualities of the biomass comprises:

- 5-10% of microalgal flour composition, preferably approximately 7%;
- 0.5-2% of sugar, preferably approximately 1%;
- 0.1-0.5% of vanilla flavoring, preferably approximately 0.25%; and
- the remainder being skimmed milk, preferably approximately 91.75%, the percentages being expressed by weight of the composition.

This composition is obtained by homogenization and then heating at 60-85° C., preferably approximately 75° C., for 2-10 minutes, preferably approximately 5 minutes.

The descriptors of the composition are evaluated by comparison with a reference composition, i.e. a tasting composition obtained from a reference microalgal flour identified as complying, i.e. of acceptable organoleptic quality (perceived as complying by said panel in all the descriptors tested).

Preferably, the reference products as presented in the following table are associated with each descriptor:

|  | Descriptors | Reference |
| --- | --- | --- |
| Appearance | Color (from light to dark) |  |
| Texture | Coating | Whole milk + 5% cream |
| Savors | Sweet | 1% sucrose |
| Flavors | Mushroom | 100 g of mushrooms in 100 ml of cold water/X 4 dilution |
|  | Cereals | 10% Ebly solution |
|  | Butter/dairy product |  |
|  | Rancid oil | 1.5% oxidized oil |
|  | Vegetable aftertaste | Very unacceptable microalgal flour composition |

At each tasting session, the products are evaluated with regard to each descriptor in comparison with the reference batch considered to be of acceptable organoleptic quality.

All the products are evaluated one after the other, on scales ranging, for example, from 1 to 9 in the following way:

Value of 1: the descriptor evaluated is not present in the product;
Value of 5: the descriptor evaluated is present in the product in exactly the same way as on the reference product of acceptable organoleptic quality;
Value of 9: the descriptor evaluated is very present in the product.

It is important to note that the reference batch of acceptable organoleptic quality is not necessarily the microalgal flour having the optimum sensory profile: it is preferably a microalgal flour composition perceived by the sensory panel as "satisfactory", in particular having a grade of 5 with regard to all the descriptors tested.

The applicant company has, moreover, established that the sensory profile of a microalgal flour composition can also be defined by the nature and the threshold of detection of specific odorous molecules, especially of particular volatile organic compounds (cf. French patent application No. 13 56113).

Indeed, it has identified a set of 13 volatile organic compounds of which the overall content in a microalgal flour composition makes it possible to determine the organoleptic quality thereof.

These 13 volatile organic compounds are the following: heptanal, 3-octen-2-one, 2,4-heptadienal, 3,5-octadien-2-one, 2,4-nonadienal, 2,4-decadienal, hexanoic acid, 2-ethylhexanoic acid, heptanoic acid, myristate-1, laurate-1, myristate-2 and geranyl acetone.

Preferably, these volatile organic compounds are sampled by solid-phase microextraction (SPME) and analyzed by gas chromatography GC, in particular by GC-MS (gas chromatography-mass spectrometry).

The content of each of the 13 volatile organic compounds is determined by the surface area of the peak of the specific ion of the SPME-GC/MS chromatogram corresponding to this volatile organic compound and is determined in comparison to that of a reference product.

The total content is obtained by adding the contents of each of the 13 compounds, preferably by determining the total surface area of the chromatography peaks corresponding to the 13 compounds. The total content can then be compared to that of a reference microalgal flour composition for which the organoleptic qualities are defined as acceptable or unacceptable.

Thus, a low total content of these 13 volatile organic compounds is associated with an optimized organoleptic quality. Conversely, a higher total content of these 13 volatile organic compounds is associated with a medium, or even poor or unacceptable, organoleptic quality.

According to one particular embodiment, the composition of flour of microalgae obtained with the process according to the invention has a total content of these 13 volatile organic compounds which is at least two times lower than that of a composition of an unacceptable organoleptic quality, preferably at least 5, 10 or 15 times lower.

According to another particular embodiment, the composition of flour of microalgae obtained with the process according to the invention has a total content of these 13 volatile organic compounds which is identical to or lower than that of a composition of an acceptable organoleptic quality.

According to one preferred embodiment, during the culturing step during which the respiratory quotient is monitored, said quotient is maintained at a value greater than 1.5, preferably greater than 1.6, more preferentially greater than 1.7 and even more preferentially greater than 1.8.

Thus, in one particular embodiment, the conditions for fermentation of the microalga, preferably *Chlorella protothecoides*, are controlled so as to maintain the respiratory quotient at a value greater than 1.5, preferably greater than 1.6, more preferentially greater than 1.7 and even more preferentially greater than 1.8, during the lipid accumulation step, and more particularly as soon as the biomass produced contains more than 25% of lipids, preferably more than 30% of lipids (% expressed by dry weight of biomass).

The respiratory quotient can be monitored continuously or semi-continuously by means of a gas analyzer which analyzes the gases escaping from the fermenter, in particular which quantifies the $CO_2$ and the $O_2$.

On the basis of these measurements, it is then possible to adjust the oxygen supply in order to modulate the respiratory quotient of the microalgae and thus to efficiently control the metabolism thereof.

Thus, in the case where the respiratory quotient is too low, the oxygen supply is decreased. In the opposite case, the oxygen supply can be increased or kept unchanged.

The oxygen supply to the fermentation medium can be carried out by any means, in particular by modulating the stirring speed, the backpressure or the oxygen concentration in the entering air (air injected into the medium).

The applicant company has also observed that the $Y_{O2/S}$ metabolic ratio (expressing the amount of oxygen consumed/amount of glucose consumed) can be used to determine whether the oxygenation is in the correct range.

Thus, according to one preferred mode, the cumulative $Y$ $O_2/S$ metabolic ratio (calculated from the beginning of the fermentation) is maintained at a value of less than 0.28, preferentially less than 0.27, more preferentially less than 0.26, in particular when the microalga is a *Chlorella protothecoides* and when the biomass produced by means of the process according to the invention has a lipid content of more than 30% by dry weight of biomass.

According to another preferred mode, the $Y$ $O_2/S$ metabolic ratio observed during the lipid accumulation phase, in particular when the biomass produced contains more than 25% of lipids, preferably more than 30% of lipids (% expressed by dry weight of biomass), is maintained at a value of less than 0.32, preferentially less than 0.28, more preferentially less than 0.27, and quite particularly preferably less than 0.26.

According to another aspect, the present invention also relates to a process for the heterotrophic culture of microalgae, comprising:
 a first culture step which allows the growth of the microalgae, and
 a second culture step which makes it possible to enrich the biomass with lipids and during which the dissolved oxygen availability in the fermenter is controlled by monitoring the respiratory quotient of said microalgae.

Preferably, in the second step, the dissolved oxygen availability is controlled by monitoring the respiratory quotient as soon as the fatty acid content is greater than 25% by dry weight of the biomass, preferably greater than 30% by dry weight of the biomass.

The embodiments described above also apply to this aspect of the invention.

According to another aspect, the present invention also relates to a process for the production of a microalgal flour composition, characterized in that it comprises the production of the microalgal biomass according to the process of the invention and the obtaining of a microalgal flour from said biomass.

The invention will be understood more clearly with the aid of the examples which follow, which are intended to be illustrative and nonlimiting.

EXAMPLES

Example 1: Production of Lipid-Rich *Chlorella Protothecoides*—Controlled Oxygenation The strain used is *Chlorella protothecoides* UTEX 250
Preculture:
500 ml of medium in a 2 l Erlenmeyer flask;
Composition of the medium:

TABLE 1

| Macroelements (g/l) | Glucose | 40 |
|---|---|---|
| | $K_2HPO_4$ | 3 |
| | $Na_2HPO_4$ | 3 |
| | $MgSO_4·7H_2O$ | 0.25 |
| | $(NH_4)_2SO_4$ | 1 |
| | Citric acid | 1 |
| | clerol FBA 3107 (antifoam) | 0.1 |
| Microelements and vitamins (mg/l) | $CaCl_2·2H_2O$ | 30 |
| | $FeSO_4·7H_2O$ | 1 |
| | $MnSO_4·1H_2O$ | 8 |
| | $CoSO_4·7H_2O$ | 0.1 |
| | $CuSO_4·5H_2O$ | 0.2 |
| | $ZnSO_4·7H_2O$ | 0.5 |
| | $H_3BO_3$ | 0.1 |
| | $Na_2MoO_4·2H_2O$ | 0.4 |
| | Thiamine HCl | 1 |
| | Biotin | 0.015 |
| | B12 | 0.01 |
| | Calcium pantothenate | 0.03 |
| | p-Aminobenzoic acid | 0.06 |

The incubation is carried out under the following conditions: time: 72 h; temperature: 28° C.; shaking: 110 rpm (Infors Multitron incubator).

The preculture is then transferred into a Sartorius 30 l fermenter.
Culture for Biomass Production:
The basic medium is the following:

TABLE 2

| Macroelements (g/l) | Glucose | 40 |
|---|---|---|
| | $KH_2PO_4$ | 0.9 |
| | $NaH_2PO_4$ | 0.7 |
| | $MgSO_4·7H_2O$ | 1.7 |
| | $(NH_4)_2SO_4$ | 0.2 |
| | clerol FBA 3107 (antifoam) | 0.3 |
| Microelements and vitamins (mg/l) | $CaCl_2·2H_2O$ | 20 |
| | $FeSO_4·7H_2O$ | 6 |
| | $MnSO_4·1H_2O$ | 20 |
| | $CoSO_4·7H_2O$ | 0.05 |
| | $CuSO_4·5H_2O$ | 0.3 |
| | $ZnSO_4·7H_2O$ | 25 |
| | $H_3BO_3$ | 7 |
| | $Na_2MoO_4·2H_2O$ | 1 |
| | Inositol | 100 |
| | Choline chloride | 100 |
| | Thiamine HCl | 3 |
| | Biotin | 0.05 |
| | B12 | 0.03 |
| | Calcium pantothenate | 0.1 |
| | p-Aminobenzoic acid | 0.1 |

The initial volume (Vi) of the fermenter is adjusted to 7 l after inoculation. It is brought to a final volume of 15-20 l.

The parameters for carrying out the various tests are the following:

TABLE 3

| | |
|---|---|
| Temperature | 28° C. |
| pH | 5.2 with 28% w/w NH$_3$ then 5N KOH |
| RQ | Test 1: Basic protocol |
| | pO$_2$ = 30% ± 5% (maintained by stirring) |
| | RQ = 1.7-1.9 |
| | Gas entering = air |
| | Test 2: Overoxygenation |
| | pO$_2$ = 120% ± 20% (maintained by stirring) |
| | RQ = 1.4-1.5 |
| | Gas entering = 90% air + 10% pure oxygen |
| | Test 3: Underoxygenation |
| | pO$_2$ = 0% |
| | RQ = 1.8-1.9 |
| | Gas entering = air |
| | Stirring maintained 10% below the level of test 1. |
| Minimum stirring | 300 RPM mini |
| Gas flow rate | 15 l/min |

When the residual concentration of glucose falls below 10 g/l, glucose in the form of a concentrated solution at 700 g/l is continuously provided so as to maintain the glucose content between 0 and 20 g/l in the fermenter.

When 1000 g of glucose have been consumed and the biomass has reached a concentration of 70 g/l, the aqueous ammonia is replaced with potassium hydroxide for pH regulation. This enables the biomass to accumulate lipids.
Results:

The tests were carried out with three levels of oxygenation. The dissolved oxygen content measured in the fermenter (pO$_2$) which is expressed as percentage of the content obtained at saturation when the fermenter is maintained at atmospheric pressure and supplied with air. A pO$_2$ of 100% corresponds to an oxygen content of approximately 7 mg/l.

Two metabolic indicators are used to quantify the impact of the level of oxygenation on the metabolism:
the Respiratory Quotient (RQ)=CO$_2$ produced/O$_2$ consumed
the yield $Y_{O2/S}$=O$_2$ consumed/glucose consumed.

They are calculated from the oxygen and CO$_2$ contents of the gas leaving the fermenter, measured using a gas analyzer.

The fatty acids were, for their part, determined by gas chromatography in the form of methyl esters after transesterification with methanolic hydrochloric acid and extraction with chloroform. The results are expressed as % distribution; the analysis is carried out via the internal standardization method.

A chromatograph (VARIAN 3800) equipped with a split-splitless injector with a tapfocus liner and a flame ionization detector was used.

An internal calibration solution containing about precisely 0.5 mg of methyl heptadecanoate per ml of methanol was prepared. The methyl heptadecanoate served as a chromatographic point of reference.

About precisely 30 mg of pre-dried sample were weighed into a 6 ml tube. 1 ml of the internal calibration solution and then 2 ml of 3N methanolic hydrochloric acid were added using a pipette with two measurement lines. The tube was then stoppered and placed in a dry bath thermostated at 110° C. for 4 h.

After cooling, about 0.5 ml of water and 0.5 ml of saturated aqueous sodium chloride were added, and the extraction was carried out with 3 times 1 ml of chloroform. The chloroform phases were recovered in a 6 ml tube with them being dried on a column containing sodium sulfate. They were concentrated under a nitrogen stream to about 1 ml and injected.

The % distribution of each fatty acid (i) was obtained by the ratio of the surface area of the peak of this fatty acid relative to the sum of the surface areas of all the peaks pinpointed on the chromatogram, from lauric acid (C12:0) to DHA (C22:6 Δ4c, 7c, 10c, 13c, 16c, 19c) inclusive, with the methyl heptadecanoate peak being excluded.

TABLE 4

| Test | Oxygenation | pO$_2$ (%) | Time (h) | Biomass (g/l) | % fatty acids | Final RQ | Final $Y_{o2/s}$ (g/g) | Cumulative $Y_{o2/s}$ (g/g) | % linoleic acid/ Σ FA |
|---|---|---|---|---|---|---|---|---|---|
| 1 | Base | 30 | 93.5 | 182 | 44.6 | 1.82 | 0.27 | 0.26 | 13.6 |
| 2 | Excess | 120 | 95.3 | 186 | 39.3 | 1.47 | 0.33 | 0.29 | 19.6 |
| 3 | Limiting | 0 | 99.1 | 188 | 43.2 | 1.86 | 0.22 | 0.24 | 6.3 |

The increase in oxygenation leads to a decrease in the respiratory quotient (increase in oxygen consumption with respect to CO$_2$ production) and an increase in the $Y_{O2/S}$ metabolic ratio (increase in oxygen consumption with respect to glucose consumption).

This is explained by the development of the fatty acid desaturation pathways which demand more oxygen than the synthesis of saturated fatty acids.

Under conditions of limited oxygenation, these desaturation pathways are not very developed, as shown by the low proportion of linoleic acid in the biomass obtained, and the value of the respiratory quotient (1.86) observed at the end of fermentation is close to the theoretical value of the oleic acid synthesis pathway:

$$35/6 C_6H_{12}O_6 + 9.5 O_2 \rightarrow C_{18}H_{34}O_2 + 17 CO_2 + 18 H_2O$$

Conversely, under overoxygenation conditions, as in test 2 where the respiratory quotient is maintained at a value of less than 1.5, that is to say much lower than the optimal value, an accumulation of linoleic acid in the biomass (19.6%) and also the appearance of off-notes (pronounced rancid savor detected by a sensory panel) are observed.

The graphs of FIGS. 1 and 2 show the evolution of the respiratory quotients of the three tests as a function of time and of the fatty acid content (by dry weight of biomass). These two representations show that the overoxygenation results in blocking of the respiratory quotient value below 1.5. On the other hand, when the oxygenation conditions are correct, the respiratory quotient during the lipid accumulation step, in particular when the fatty acid content is at least 25% by dry weight of biomass, is greater than 1.5.

Example 2: Sensory Evaluation of the 3 Batches Produced in Example 1

In this example, the applicant company proposes to determine the sensory quality of microalgal flours prepared from the 3 batches produced in example 1, said flours prepared from biomasses that have been ground and dried according to the method described in patent application WO 2010/12093.

The applicant company defined, in French patent application No. 13 56113, a very simple tasting matrix which makes it possible to make an organoleptic evaluation similar to that obtained with much more complex and very different recipes, such as an ice cream or a brioche. The evaluation with this tasting matrix is much more precise or accurate than that carried out with a simple aqueous solution, which has proved to be incapable of predicting the organoleptic qualities of microalgal flour compositions in an ice cream, for example.

The microalgal flour tasting composition thus comprises:
7% of microalgal flour composition;
1% of sugar;
0.25% of vanilla flavoring; and
91.75% of skimmed milk,
the percentages being expressed by weight of the composition.

This composition is subsequently homogenized and then heated at 75° C. for 5 minutes.

A set of 15 individuals is brought together in order to evaluate descriptors of several microalgal flour compositions in comparison with a sample of reference microalgal flour identified as complying, that is to say of acceptable organoleptic quality (reference batch), i.e. a batch of microalgal flour perceived as complying by said panel in all of the descriptors tested, this being a standard internal to the panel.

The reference products as presented in table 5 below are associated with each descriptor:

TABLE 5

| | Descriptors | Reference |
|---|---|---|
| Appearance | Color (from light to dark) | |
| Texture | Coating | Whole milk + 5% cream |
| Savors | Sweet | 1% sucrose |
| Flavors | Mushroom | 100 g of mushrooms in 100 ml of cold water/X 4 dilution |
| | Cereals | 10% Ebly solution |
| | Butter/dairy product | |
| | Rancid oil | 1.5% oxidized oil |
| | Vegetable aftertaste | Very unacceptable microalgal flour composition |

At each tasting session, the products are evaluated with regard to each descriptor in comparison with the reference batch considered to be of acceptable organoleptic quality.

All the products are evaluated one after the other, on scales ranging from 1 to 9 in the following way:

Value of 1: the descriptor evaluated is not present in the product;

Value of 5: the descriptor evaluated is present in the product in exactly the same way as on the reference product of acceptable organoleptic quality;

Value of 9: the descriptor evaluated is very present in the product.

The reference batch of acceptable organoleptic quality is a microalgal flour composition perceived by the sensory panel as "satisfactory", that is to say having a grade of 5 with regard to all the descriptors tested.

Data Processing Software

The analyses were carried out using the R software (freely sold):
R version 2.14.1 (2011-12-22)
Copyright (C) 2011 The R Foundation for Statistical Computing
ISBN 3-900051-07-0
Platform: i386-pc-mingw32/i386 (32-bit)

The software is a working environment which requires the loading of modules containing the calculation functions.

The modules used in this study are the following:
For the PCA: Package FactoMineR version 1.19
For the ANOVA: Package car version 2.0-12
For the Linear Regression: Package stats version 2.14.1

Data Processing:

Analyses of variance (ANOVAs) are carried out in order to evaluate the discriminating capacity of the descriptors (descriptors of which the p-value associated with the Fisher test—type-1 ANOVA—is less than 0.20 for the Composition effect in the model descriptor~composition+judge).

The "composition" effect is interpreted as the discriminating capacity of the descriptors: if there is no effect (Critical Probability >0.20), the compositions were not discriminated according to this criterion. The smaller the critical probability, the more discriminating is the descriptor.

A principal component analysis (PCA) is then carried out in order to obtain sensory mapping of the compositions, and also a simultaneous representation of all the compositions regarding all the descriptors.

The 3 batches of example 1 were analyzed according to the method described above.

Two examples regarding the descriptors "butter/dairy products" and "vegetable aftertaste" are presented here.

| "Vegetable aftertaste" Analysis of variance table | | | | | |
|---|---|---|---|---|---|
| | Df | Sum Sq | Mean Sq | F value | Pr(>F) |
| Composition | 9 | 109.693 | 12.1881 | 18.2423 | <2e−16 |
| Judge | 13 | 18.732 | 1.4409 | 2.1566 | 0.01298 |
| Residues | 185 | 123.603 | 0.6681 | — | |

| "Butter/dairy products" Analysis of variance table | | | | | |
|---|---|---|---|---|---|
| | Df | Sum Sq | Mean Sq | F value | Pr(>F) |
| Composition | 9 | 8.292 | 0.92131 | 1.4530 | 0.1699 |
| Judge | 13 | 8.235 | 0.63347 | 0.9991 | 0.4547 |
| Residues | 160 | 101.451 | 0.63407 | — | |

It appears that the critical probabilities associated with the composition effect for the 2 descriptors studied are less than 0.2: the 2 descriptors are therefore discriminating. The critical probability is smaller with regard to the "vegetable aftertaste" descriptor than with regard to the "butter/dairy products" descriptor, thereby signifying that a greater difference is observed between the compositions with regard to the first criterion than with regard to the second.

Below is a table summing up the critical probabilities obtained for the composition and judge effects for all the descriptors.

TABLE 6

|  | Composition | Judge |
| --- | --- | --- |
| Yellow color | 0.00 | 0.05 |
| Vegetable aftertaste | 0.00 | 0.31 |
| Rancid oil taste | 1 | 1 |
| Coating | 0.60 | 0.03 |
| Cereals | 0.03 | 0.36 |
| Mushrooms | 0.12 | 0.01 |
| Sweet | 0.50 | 0.09 |
| Dairy products | 0.59 | 0.87 |

The yellow, vegetable aftertaste, cereals and mushroom descriptors are discriminating; they are all kept for establishing the PCA.

Since the aromatic is an essential criterion of the compositions, the PCA was carried out regarding the descriptors relating to the flavors only (mushroom, cereals, vegetable aftertaste, dairy product, rancid). The graphic representation of this PCA is provided in FIG. 3 and FIG. 4.

This method makes it possible to establish a classification of the organoleptic quality of the various microalgal flours produced from the 3 tests of example 1. Thus, the flours obtained from tests 1 and 3 (base or limiting oxygenation) have similar organoleptic qualities which are much better than those of the flours obtained from test 2 (excess oxygenation).

This is because the oxygenation conditions defined as "in excess" lead to greater mushroom and cereal flavors and to a vegetable aftertaste. These conditions should therefore be banned in order to guarantee the neutrality of the taste of the product.

The oxygenation conditions defined as "limiting" provide a product which is slightly more yellow but not very different in terms of taste than the product obtained under the oxygenation conditions defined as "base", and which is itself very close to the reference product.

Example 3: Analysis of the Volatile Organic Compounds (VOCs) Associated with Unacceptable Off-Note Organoleptic Classifications in the 3 Batches of Compositions of Flour of Microalgae Obtained from Example 1

In order to carry out the SPME/GC-MS analysis of the 3 batches of compositions of flour of microalgae obtained from the biomasses produced in example 1, the process is carried out as follows.

A test specimen of 3 g of sample is introduced into a sealed SPME flask (20 ml) and incubated at 60° C. for 15 min and then extracted at 60° C. for 45 min with a DVB/CAR/PDMS (abbreviation for divinylbenzene/-carboxen/polydimethylsiloxane, df 50/30 μm) SPME fiber.

The volatile organic compounds extracted are desorbed in the injector of the TSQ GC-MS system from Thermo Scientific, and then separated on a CPwax52 (60 m×0.25 mm, 0.25 μm) column with helium gas at 1.5 ml/min.

The temperature program is: 50° C. isotherm for 3 min, then programming at 5° C./minute up to 230° C., then isotherm for 20 min.

The detection is carried out by electron impact (EI) mass spectrometry and the compounds are identified by comparison with EI spectra of the NIST library.

As indicated above, the applicant company identified, in French patent application No. 13 56113, 13 compounds making it possible to define the organoleptic quality of the microalgal flours obtained according to the invention.

These 13 compounds are the following: heptanal, 3-octen-2-one, 2,4-heptadienal, 3,5-octadien-2-one, 2,4-nonadienal, 2,4-decadienal, hexanoic acid, 2-ethylhexanoic acid, heptanoic acid, myristate-1, laurate-1, myristate-2, and geranyl acetone. Represented here therefore are the families of diunsaturated aldehydes, unsaturated ketones, carboxylic acids and carboxylic acid derivatives.

The olfactory thresholds in water, attributed to these 13 compounds, are presented in table 7 below.

TABLE 7

|  | Olfactory threshold in water (ppb) |
| --- | --- |
| 2,4-decadienal | 0.07 |
| 2,4-heptadienal* | 0.1 |
| 2,4-nonadienal | 0.01 |
| 3,5-octadien-2-one* | 1 |
| 3-octen-2-one* | 1 |
| heptanal | 3 |
| 2-ethylhexanoic acid* | 1000 |
| heptanoic acid | 3000 |
| hexanoic acid | 3000 |
| geranyl acetone | 60 |
| myristate-1* | 1 |
| laurate-1* | 1 |
| myristate-2* | 1 |

*Olfactory threshold established by the applicant company

FIG. 5 presents the individual flavor values of each of the 13 compounds for the 3 batches of example 1.

It appears that:
- 4 principal compounds have all the flavors detected: 2,4-heptadienal, 3,5-octadien-2-one, 2,4-nonadienal and 2,4-decadienal, which is in accordance with what is known in the prior art as unsaturated fatty acid oxidative degradation (peroxidation) product;
- the 2,4-heptadienal and 3,5-octadien-2-one content is relatively lower for the "base" and "limiting" batches compared with the "excess" batch, the "limiting" batch having the lowest content;
- the 2,4-nonadienal and 2,4-decadienal content is relatively lower for the "base" and "limiting" batches compared with the "excess" batch, the "base" batch having the lowest content.

These results reflect a better organoleptic quality of the "limiting" and "base" batches.

Table 8 below presents the sum of the individual flavor values of these 13 compounds, therefore the total flavor value, determined from the relative contents of the 13 compounds and their olfactory thresholds:

$FV\ total = \Sigma FVx$ (sum of the individual $FVs$), with FVx=Concentration of the compound x/olfactory threshold of the compound x for each of the batches of microalgal flour compositions (value of 100% assigned to the "Excess" batch).

TABLE 8

|  | Total flavor value (%) |
| --- | --- |
| Base | 5.6 |
| Excess | 100 |
| Limiting | 6 |

Here again, this GC/MS analysis also makes it possible to demonstrate that the flours obtained from tests 1 and 3 (base or limiting oxygenation) of example 1 have similar organoleptic qualities which are much better than those of the flours obtained from test 2 (excess oxygenation).

Figure 1:
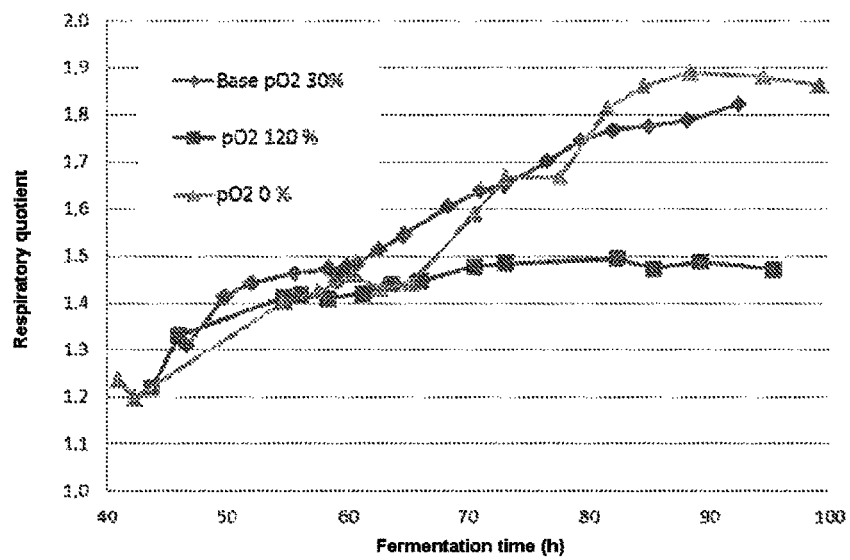
FIG. 1: Evolution of the respiratory quotients as a function of fermentation time (in hours) for tests 1 (Base $pO_2$ 30%), 2 ($pO_2$ 0%) and 3 ($pO_2$ 120%).
Figure 2:
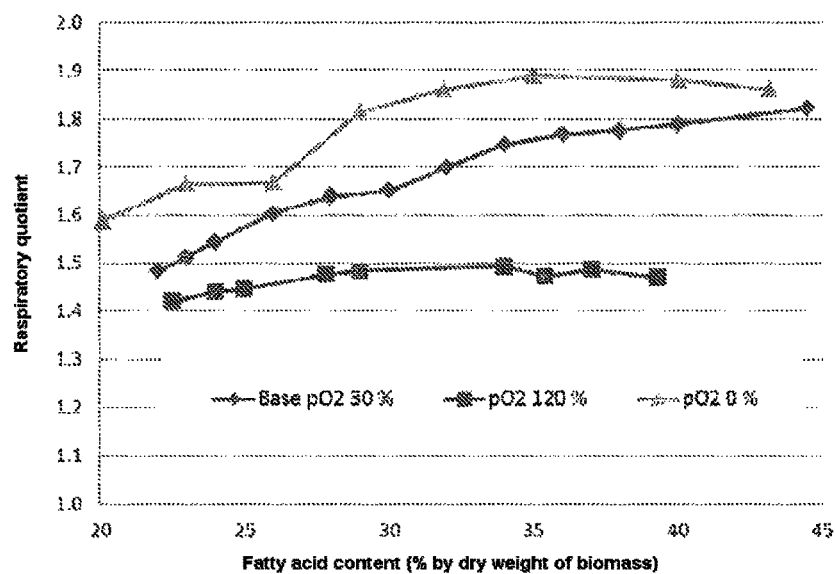
FIG. 2: Evolution of the respiratory quotients as a function of fatty acid content for tests 1 (Base $pO_2$ 30%), 2 ($pO_2$ 0%) and 3 ($pO_2$ 120%).
Figure 3:
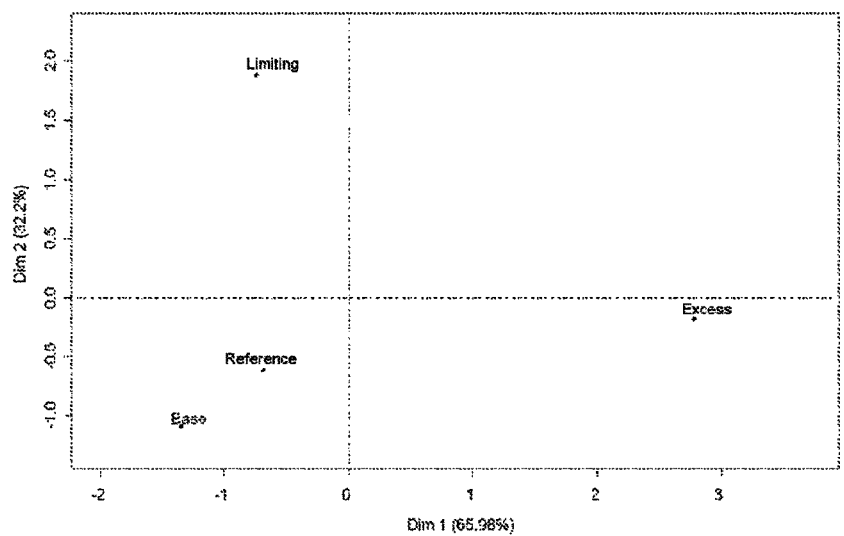
FIG. 3: Graphic representation of the various batches (cloud of points) of the PCA.
Figure 4:
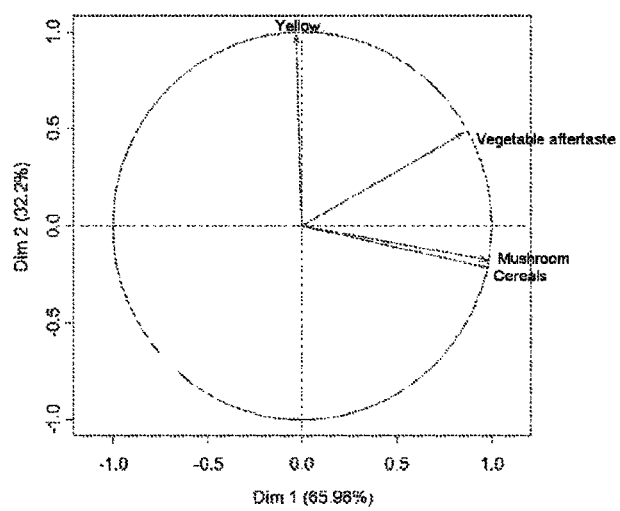
FIG. 4: Circle of correlation of the PCA representing the aromatic profiles of the various batches.
Figure 5:
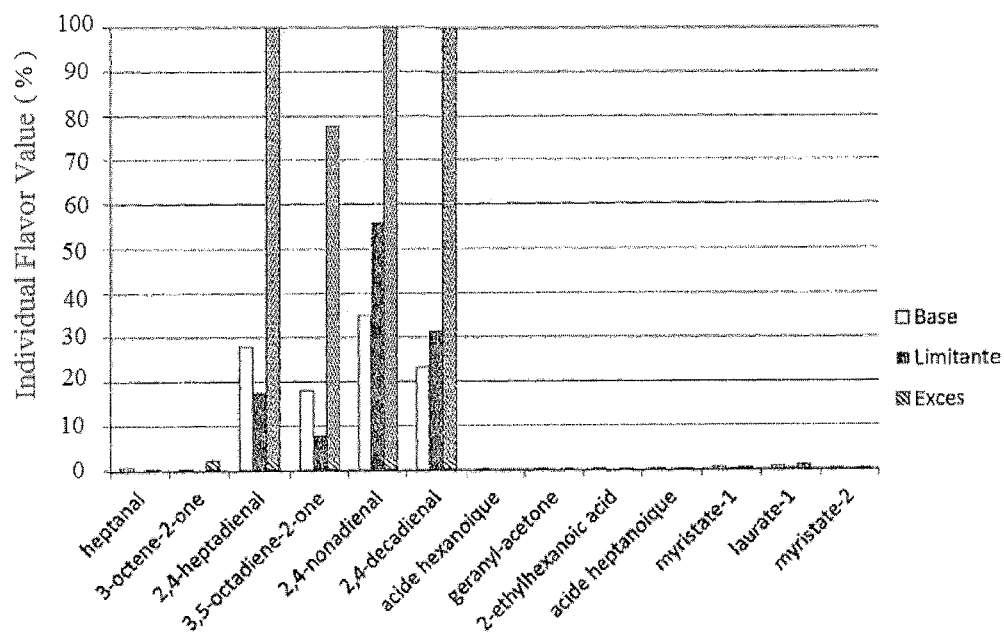
FIG. 5: Individual flavor values of the 3 production batches.

The invention claimed is:

1. A process for the fermentative production of a biomass of lipid-rich microalgae of genus *Chlorella* in a fermenter comprising, culturing said microalgae in a medium under heterotrophic conditions in at least one culturing stage to produce a biomass; controlling dissolved oxygen availability in the fermenter during said at least one culturing stage by monitoring a respiratory quotient RQ and adjusting oxygen availability to maintain said RQ at a value of between 1.5 and about 1.9 when a lipid content of said biomass is more than 25% by dry weight, wherein RQ is defined as an amount of $CO_2$ produced relative to an amount of $O_2$ consumed per unit of time, and wherein the biomass, comprises less than 18% linoleic acid by weight relative to a total weight of fatty acids in the dry biomass.

2. The process according to claim 1, wherein the fermentative production is carried out on an industrial scale.

3. The process according to claim 1, wherein said microalgae is selected from the group consisting of *Chlorella vulgaris*, *Chlorella sorokiniana* and *Chlorella protothecoides*.

4. The process according to claim 1, wherein the microalgae is *Chlorella protothecoides*.

5. The process according to claim 1, wherein the biomass produced by means of said process has a lipid content of more than 30% by dry weight of biomass.

6. The process according to claim 1, wherein said at least one culturing stage comprises a lipid accumulation phase.

7. The process according to claim 1, wherein the dissolved oxygen availability in the fermenter is ensured by monitoring the respiratory quotient as soon as the biomass has a lipid content of more than 30% by dry weight of biomass.

8. The process according to claim 1, wherein a cumulative metabolic ratio $Y_{O2/S}$ calculated from the beginning of the fermentation is maintained at a value of less than 0.28.

9. The process according to claim 6, wherein said metabolic ratio $Y_{O2/S}$ is observed during the lipid accumulation stage and is maintained at a value of less than 0.28 when the biomass contains more than 25% lipids by dry weight of biomass.

10. The process according to claim 1, wherein the biomass comprises volatile organic compounds comprising saturated and di-unsaturated aldehydes, unsaturated ketones, and carboxylic acids and derivatives.

11. The process according to claim 1, wherein a content of linoleic acid in the biomass produced is less than 14% by weight relative to a total weight of fatty acids in the dry biomass.

12. The process according to claim 1, wherein the respiratory quotient is monitored using a gas analyzer.

13. The process according to claim 1, wherein the oxygen availability is controlled by varying oxygen supplied to the fermentation medium by modulating stirring speed, back pressure or oxygen concentration.

* * * * *

UNITED STATES PATENT AND TRADEMARK OFFICE
CERTIFICATE OF CORRECTION

PATENT NO. : 10,351,814 B2
APPLICATION NO. : 14/913383
DATED : July 16, 2019
INVENTOR(S) : Sylvain Delaroche et al.

Page 1 of 1

It is certified that error appears in the above-identified patent and that said Letters Patent is hereby corrected as shown below:

In the Claims

In Line 1 of Claim 9 (Column 18, Line 17), please change the claim dependency from "claim 6" to --claim 8--.

Signed and Sealed this
Third Day of September, 2019

Andrei Iancu
*Director of the United States Patent and Trademark Office*